US008435480B2

(12) United States Patent
Han et al.

(10) Patent No.: US 8,435,480 B2
(45) Date of Patent: May 7, 2013

(54) METHOD FOR SYNTHESIZING ONE-DIMENSIONAL HELICAL NANOPOROUS STRUCTURES AND METHOD FOR SYNTHESIZING GLYCINE-DERIVED SURFACTANT FOR SYNTHESIZING HELICAL NANOPOROUS STRUCTURES

(75) Inventors: Sang Cheol Han, Busan (KR); Yang Kim, Busan (KR); Chung Kwon Park, Busan (KR)

(73) Assignee: Thermolon Korea Co., Ltd. (KR)

( * ) Notice: Subject to any disclaimer, the term of this patent is extended or adjusted under 35 U.S.C. 154(b) by 152 days.

(21) Appl. No.: 12/921,457

(22) PCT Filed: Apr. 10, 2009

(86) PCT No.: PCT/KR2009/001869
§ 371 (c)(1),
(2), (4) Date: Sep. 8, 2010

(87) PCT Pub. No.: WO2009/131324
PCT Pub. Date: Oct. 29, 2009

(65) Prior Publication Data
US 2011/0039682 A1 Feb. 17, 2011

(30) Foreign Application Priority Data

Apr. 25, 2008 (KR) .................. 10-2008-0038509
Apr. 29, 2008 (KR) .................. 10-2008-0039725

(51) Int. Cl.
*C01B 13/14* (2006.01)
*C01B 33/12* (2006.01)
*C01G 25/02* (2006.01)
*C01G 27/02* (2006.01)
*C01G 23/047* (2006.01)
*C01G 17/02* (2006.01)
*C01G 19/02* (2006.01)
*C01G 9/02* (2006.01)

(52) U.S. Cl.
USPC ........ 423/592.1; 423/338; 423/608; 423/610; 423/612; 423/618; 423/622; 977/768

(58) Field of Classification Search .................. 423/335, 423/608, 610–612, 618, 622; 501/80; 977/700, 977/768
See application file for complete search history.

(56) References Cited

U.S. PATENT DOCUMENTS 7,291,215 B2    11/2007  Oike et al.
2008/0038492 A1*  2/2008  Huang et al. ................. 428/34.1
(Continued)

FOREIGN PATENT DOCUMENTS

DE         296093 A5      11/1991
JP       2003-246615 A     9/2003

OTHER PUBLICATIONS

Che et al., "Synthesis and characterization of chiral mesoporous silica", Nature, vol. 429, May 20, 2004, pp. 281-284.*

(Continued)

*Primary Examiner* — Colleen Dunn
*Assistant Examiner* — Anthony J Zimmer
(74) *Attorney, Agent, or Firm* — John K. Park; Park Law Firm

(57) ABSTRACT

Disclosed herein are a method for synthesizing one-dimensional helical mesoporous structure, in which a self-assembled structure of a glycine-derived surfactant is used as a template at room temperature to synthesize the one-dimensional helical mesoporous silica structures having a uniform pore size and a method for synthesizing a glycine-derived surfactant for synthesizing the helical nanoporous structures, in which relatively expensive surfactant can be easily recovered using an organic solvent and reused, which provides economical and environment friendly effects and the glycine-derived surfactant is synthesized by homogeneously heating a reaction product of glycine and phthalic anhydride by dielectric heating with irradiation of microwave, whereby it is possible to realize high yield of the glycine-derived surfactant, shortened synthesis time and increase in energy efficiency, leading to improvement in productivity and reduction in production cost.

7 Claims, 3 Drawing Sheets

U.S. PATENT DOCUMENTS

2011/0056020 A1* 3/2011 Al-Saif .............................. 5/420
2011/0189071 A1* 8/2011 Ying et al. .................... 423/335

OTHER PUBLICATIONS

Tanev et al., "A Neutral Templating Route to Mesoporous Molecular Sieves", Science 267, Feb. 10, 1995, pp. 865-867.*

Kresge et al., "Ordered mesoporous molecular sieves synthesized by a liquid-crystal template mechanism", Nature, 359, p. 710-, Oct. 22, 1992.*

Han et al., "Entropy-Driven Helical Mesostructure Formation with Achiral Cationic Surfactant Templates", Advanced Materials 2007, 19, 2454-2459.*

Yang et al., "Formation of Helical Hybrid Silica Bundles", Chemistry of Materials 16 (20), Oct. 5, 2004, 3791-3793.*

Antunes, R. et al., New Phthalimide Derivatives with Potent Analgesic Activity, Bioorganic & Medicinal Chemistry Letters, 1998, pp. 3071-3076, vol. 8.

Vidal, T. et al., Re-examination of Microwave-Induced Synthesis of Phthalimides, Tetrahedron, 2000, pp. 5473-5478, vol. 56.

* cited by examiner

METHOD FOR SYNTHESIZING ONE-DIMENSIONAL HELICAL NANOPOROUS STRUCTURES AND METHOD FOR SYNTHESIZING GLYCINE-DERIVED SURFACTANT FOR SYNTHESIZING HELICAL NANOPOROUS STRUCTURES

TECHNICAL FIELD

The present invention relates to a method for synthesizing one-dimensional helical nanoporous structures, in which a structure formed by self-assembly of a glycine-derived surfactant in a room temperature environment is used as a template to synthesize silica helical mesoporous structures and the glycine-derived surfactant is synthesized using microwaves, and a method for synthesizing a glycine-derived surfactant for synthesizing helical nanoporous structures.

BACKGROUND ART

Generally, the methods for preparing nanoporous materials of an inorganic compound such as silica using an organic compound as a template are widely used in order to synthesize nanoporous materials using a template. Particularly, since the method for synthesizing nanoporous silica using a surfactant capable of forming micells as a template, among organic compounds, was discovered, there have been many reports in connection with application to chemistry, biochemistry, optical science and electrical industry. Such inorganic compounds possess useful properties applied to molecule sensors, agents for compound separation, chromatography agents, adsorbing agents, catalysts and functional devices such as light emitting devices and thus, are researched by many laboratories. Specifically, the sol-gel template method (SGTM) is most commonly used to synthesize a wide range of nano-sized inorganic compounds having various structures, which are synthesized by ionic bond or hydrogen bond between proper cationic parts of assembled organic molecules and adsorbing inorganic compound.

Many research groups in the world are synthesizing nano-sized structures with various sizes and structures by using such surfactants. Particularly, 2-amino-N-dodecylacetamide which is one of the glycine-derived surfactant having the peptide structure is applied in the medical field. The surfactants of this type are commonly synthesized by attaching an amine protector such as butyloxycarbonyl (BOC) and fluorenylmethyloxycarbonyl (Fmoc) to an end of an amine to lower the reactivity. Thus, the synthesis is simple, but the used agents such as BOC and Fmoc are rather expensive. On the other hand, the synthesis method using phthalic anhydride is advantageously cheap and can realize mass production of surfactants. However, this method needs a large amount of aromatic compounds, synthesizing apparatus is complex and a large amount of energy is consumed.

Thus, for the synthesis of 2-amino-N-dodecylacetamide which is one of the glycine-derived surfactant synthesized by the conventional method, the peptide synthesizing agent may be used in those fields including the value-added medicinal fields, where the agent is used in a tiny amount, but is not suitable for a template to synthesize commercially applicable nanostructures where it is used in a large amount. Accordingly, in order to solve such problems, researches have been diversely attempted to develop new synthesis.

As a method for synthesizing nanostructures using a surfactant, Kresge et al. have synthesized nanosilica structures (MCM-41) using alkylammonium bromide (See, Kresge C T, Leonowicz M E, Roth W J, Vartuli J, Beck J S, Nature, 359, 710, 1992). By this method, it was possible to produce hexagonal nanostructures having a pore size of 2 to 3 nm. However, these structures had problems that they should be synthesized by the hydrothermal method under strong basic conditions and were easily collapsed in an aqueous solution.

Pinnavaia et al. have synthesized silica nanostructures (HMS) using an alkylamine($C_nH_{2n+1}NH_2$) which was electrically neutral (Peter T. Taney and Thomas J. Pinnavaia, Science, 1995, 267, 865-867). This method could produce nanostructures with cumulated pores, which had a pore size of 2 to 3 nm, at room temperature. However, these structures were physically weak and showed poor alignment. The same research group synthesized very stable elliptical mesoporous structures (MSU-G) using a surfactant ($C_nH_{2n+1}NH(CH_2)_2NH_2$) which had an electrically neutral secondary amine group (S. S. Kim, T. J. Pinnavaia, Science, 1998, 282:1302-1305). Owing to the amine group with the double bond, the elliptical structures were self-assembled. Also, through the self-assembly, strong hydrogen bonds were formed, and the self-assembled structures were not broken down even at the high temperature in the hydrothermal synthesis (for 100 to 150 hours), whereby thermal stability similar to zeolite was secured. As compared to the existing mesoporous materials, these structures showed a high $Q_4$ (the whole single bond of Si being bonded)/$Q_3$. Further, this group reported that the structures which were synthesized using the electrically neutral amine group showed higher thermal stability than a surfactant having ionic properties. However, these structures were found to have problems in alignment and energy consumption caused by heating at a thigh temperature.

Also, Che et al. have synthesized N-acyl-L-alanine which is an amino acid surfactant and synthesized helical mesoporous structures using the amino acid surfactant as a template and an amino silane copolymer as a co-structured directing agent (CSDA), in which the mesoporous structure has a pore size of about 2.2 nm (S. Che, Z. Liu, T. Ohsuna, K. Sakamoto, O. Terasaki and T. Tatsumi Nature 429, 281-284). However, this synthesis had problems in that the synthesis cannot be reproduced since it used copolymers which made the method complicated, the pore size was small and safety was not secured.

As described above, various methods for synthesizing silica nanostructures using a surfactant have been disclosed and the present inventors also have synthesized one-dimensional silica helical mesoporous structures by using a glycine-derived surfactant and adjusting the temperature of the gelling synthesis. Thus, the method has been completed.

DISCLOSURE OF INVENTION

Technical Problem

Accordingly, the present invention has been made in order to solve the problems occurring in the prior art, and it is an object of the present invention to provide a method for synthesizing one-dimensional helical nanoporous structures, which can prepare a wide spectrum of nano-sized organic and inorganic structures having various structures by the sol-gel template method (SGTM) using a glycine-derived surfactant.

Particularly, it is an object of the present invention to provide a method for synthesizing mesoporous silica helical structures using the difference of self-assembly according to the temperature of a peptide surfactant, which have a higher alignment and crystallinity than general mesoporous silica structures.

Also, it is another object of the present invention to provide a method for synthesizing one-dimensional helical nanoporous structures, in which a glycine-derived surfactant which is used as a template can be readily recovered for recycling and thus, improves the process economically and environment friendly.

It is a further object of the present invention to provide a method for synthesizing a glycine-derived surfactant to be used for synthesizing helical nanoporous structures, in which the glycine-derived surfactant is synthesized by homogeneously heating a reaction product of glycine and phthalic anhydride by dielectric heating with irradiation of microwave, whereby it is possible to realize high yield of the glycine-derived surfactant, shortened synthesis time and increase in energy efficiency, leading to improvement in productivity and reduction in production cost.

Technical Solution

To accomplish the above objects, in one aspect, the present invention provides a method for synthesizing one-dimensional helical nanoporous structures, the method comprising the steps of: (1) heating an aqueous solution, obtained by adding a template to water, until the aqueous solution becomes transparent; (2) adding a ceramic precursor to the template-containing aqueous solution of step (1), and then heating the aqueous solution until it becomes transparent; (3) allowing the heated aqueous solution of step (2) to stand to form a gelled mixture; (4) washing the gelled mixture of step (3) with alcohol to remove the template; and (5) calcining the washed mixture of step (4) from which the alcohol and the template have been removed.

In the step (1), the template has a glycine-derived surfactant having the following chemical structure:

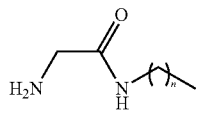

wherein n is preferably an integer ranging from 7 to 15.

In another aspect, the present invention also provides a method for synthesizing a glycine-derived surfactant for synthesizing one-dimensional helical nanoporous structures, the method comprising the steps of: (G1) irradiating a reaction product of glycine (a) and phthalic anhydride (b) with microwaves to produce 2-(1,3-dioxoisoindolin-2-yl)acetic acid (compound 1); (G2) adding $SOCl_2$ to the compound 1 of step (G1) to produce 2-(1,3-dioxoisoindolin-2-yl)acetic chloride (compound 2); (G3) allowing the compound of step (G2) to react with alkylamine so as to product N-alkyl-2-(1,3-dioxoisoindolin-2-yl)acetamide (compound 3); and (G4) adding ethanol and $NH_2NH_2$ to the compound 3 of step (G3) to form a mixture, and then heating the mixture to synthesize 2-amino-N-alkylacetamide (compound 4).

Advantageous Effects

According to the present invention, the one-dimensional helical nanoporous structures are synthesized by using a glycine-derived surfactant as a template in an aqueous solution state in a neutral condition at room temperature. Therefore, the relatively expensive surfactant can be easily recovered and reused, which provides economical and environment friendly effects. Also, the glycine-derived surfactant is synthesized by irradiating a reaction product of glycine and phthalic anhydride with microwaves, whereby it is possible to realize high yield of the glycine-derived surfactant, shortened synthesis time and increase in energy efficiency, leading to improvement in productivity and reduction in production cost.

BEST MODE FOR CARRYING OUT THE INVENTION

Figure 1:
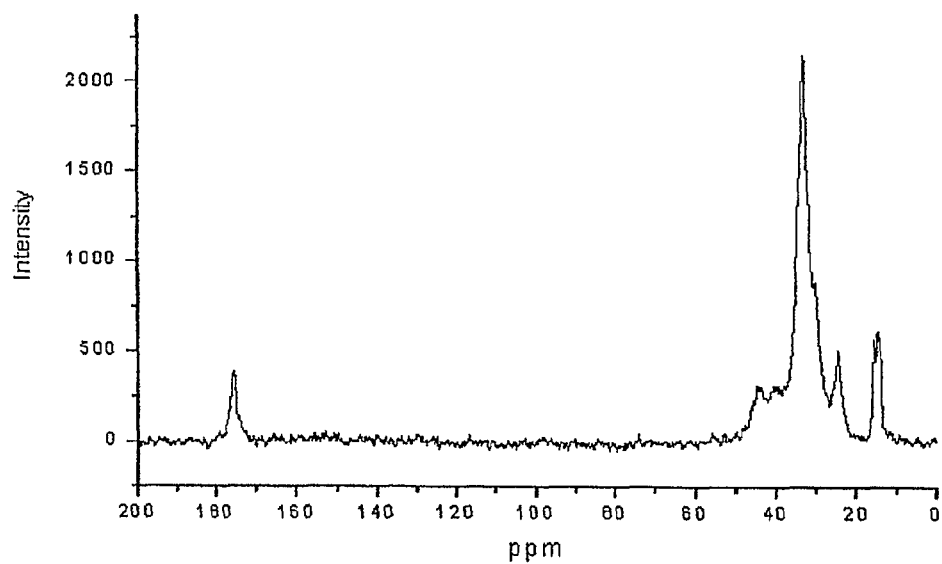
FIG. 1 is a graph showing the $^1$H-NMR result of 2-amino-N-dodecylacetamide.

In one aspect, the present invention relates to a method for synthesizing one-dimensional helical nanoporous structures, which comprises the steps of: (1) heating an aqueous solution, obtained by adding a template to water, until the aqueous solution becomes transparent; (2) adding a ceramic precursor to the template-containing aqueous solution of step 1), and then heating the aqueous solution until it becomes transparent; (3) allowing the heated aqueous solution of step 2) to stand to form a gelled mixture; (4) washing the gelled mixture of step 3) with alcohol to remove the template; and (5) calcining the washed mixture of step 4) from which the alcohol and the template have been removed.

In the step (1), the template which is used to form the nanostructure is a gel-generator having the following formula 4, which is a glycine-derived surfactant.

In this step, the glycine-derived surfactant is added to water and heated for dissolution. 1 mmol of glycine-derived surfactant is mixed with 15 to 25 ml of water and heated at a temperature of 60±1° C., until the aqueous solution becomes transparent. Here, if the amount of water mixed with 1 mmol of the glycine-derived surfactant is less than 15 ml or the heating temperature is lower than the lower limit of the described range, the dissolution may not be accomplished. If the amount of water mixed with 1 mmol of the glycine-derived surfactant is more than 25 ml or the heating temperature is higher than the upper limit of the described range, the self-assembly may not be performed, causing deterioration of yield.

The glycine-derived surfactant is a compound of the following formula 4:

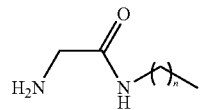

wherein n is preferably an integer ranging from 7 to 15.

Also, in the step 2), the ceramic precursor is added to the transparent aqueous solution of the surfactant and then, the solution is reheated at a temperature of 60±1° C. until it becomes transparent. The ceramic precursor is preferably added in an amount of 4 to 10 mmol per mmol of the glycine-derived surfactant. If the ceramic precursor is added in an amount of less than 4 mmol, the thickness of the silica film can be too thin. If the ceramic precursor is added in an amount of more than 10 mmol, the thickness of the silica outer layer can be too thick, generating another structure.

In addition, preferably, the ceramic precursor is one or more selected from the group consisting of silica precursors, including TEOS (tetraethoxysilane), TBOS (tetrabutyl orthosilicate), TMOS (teramethoxysilane) and $SiCl_4$ (tetrchlorosilane), $TiO_2$ precursors, including titanium(IV) butoxide, titanium(IV) isopropoxide and titanium(IV) chloride, $SnO_2$ precursors, including tin(IV) chloride and tin(IV) tert-butoxide, $ZnO_2$ precursors, including zinc acetate and zinc chloride, and $ZrO_2$ precursors, including zirconium(IV) t-butoxide, zirconium(IV) chloride, zirconium(IV) ethoxide and zirconium(IV) propoxide.

In the step (3), the heated ceramic precursor-containing aqueous solution of the surfactant is allowed to stand for 3 days at room temperature. While the heated ceramic precursor-containing aqueous solution of the surfactant is kept in the static condition for 3 days, the surfactant molecules form the gelled mixture by the self-assembly together with the ceramic precursor.

In the step (4), the gelled mixture of the ceramic precursor is washed with an alcohol to remove the surfactant and the alcohol is then, removed. By the self-assembly of the surfactant molecules, the helical nanostructures are formed on the ceramic precursor to contain mesopores having a pore size of 2 to 5 nm. The alcohol used in the present invention is any one selected from the group consisting of methyl alcohol, ethyl alcohol, propyl alcohol and butyl alcohol and is preferably added in an amount of 10 to 30 ml per equivalent weight (1 mmol). If the alcohol is added in an amount of less than 10 ml, the glycine-derived surfactant cannot be sufficiently recovered owing to lack of the alcohol. If the alcohol is added in an amount of more than 30 ml, it is extravagant.

In the step (5), the mixture of the ceramic precursor from which the alcohol and the template have been removed is calcined at a temperature of 500 to 600° C. to shape the mesoporous silica helical structures. If the calcination temperature is less than 500° C., the template which has not removed can be may be left over. If the calcination temperature exceeds the structures may be collapsed.

Therefore, the mesoporous silica helical structures synthesized by the above-described method have a higher alignment and crystallinity than general mesoporous silica structures. Also, since the glycine-derived surfactant which is used as a template in the synthesis can be readily recovered for recycling, the present invention provides an economical and environment friendly method.

Also, in another aspect, the present invention relates to a method for synthesizing a glycine-derived surfactant to be used for synthesizing the one-dimensional helical nanoporous structures.

Firstly, the method for synthesizing the glycine-derived surfactant by using microwaves will be described in detail with reference to the following reaction scheme.

The present invention is directed to a method for synthesizing a glycine-derived surfactant for synthesizing one-dimensional helical nanoporous structures, the method comprising the steps of:

(G1) irradiating a reaction product of glycine (a) and phthalic anhydride (b) with microwaves to produce 2-(1,3-dioxoisoindolin-2-yl)acetic acid (compound 1);

(G2) adding $SOCl_2$ to the compound 1 of step (G1) to produce 2-(1,3-dioxoisoindolin-2-yl)acetic chloride (compound 2);

(G3) allowing the compound of step (G2) to react with alkylamine so as to product N-alkyl-2-(1,3-dioxoisoindolin-2-yl)acetamide (compound 3); and (G4) adding ethanol and $NH_2NH_2$ to the compound 3 of step (G3) to form a mixture, and then heating the mixture to synthesize 2-amino-N-alkylacetamide (compound 4).

The glycine-derived surfactant is synthesized through the (G1) to (G4) steps of the following Reaction Scheme 1.

Therefore, according to the present invention, in the (G1) step, the glycine-derived surfactant is synthesized by irradiating glycine and phthalic anhydride with microwaves.

[Reaction Scheme 1]

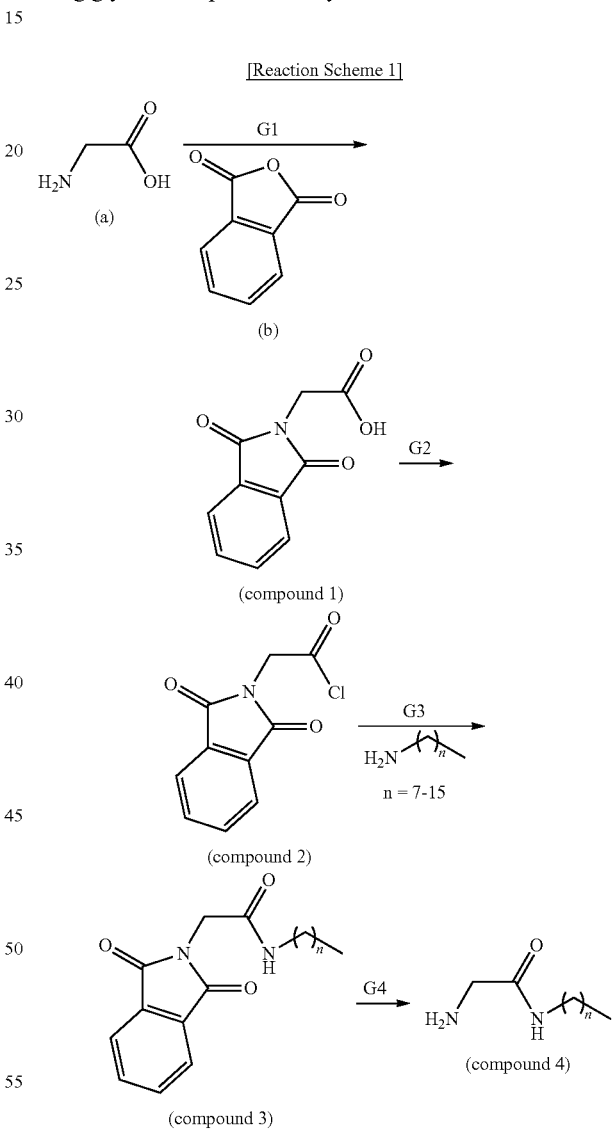

According to the present invention, since glycine (a) and phthalic anhydride (b) are reacted with each other by irradiation of microwaves in the (G1) step, it is possible to increase the production yield of the glycine-derived surfactant.

In the present invention, the (G1) step is a step to produce 2-(1,3-dioxoisoindolin-2-yl)acetic acid (compound 1) by irradiating a reaction product of glycine (compound a) and phthalic anhydride (compound b) with microwaves. In this step, glycine and phthalic anhydride undergo the co-condensation reaction to produce the compound 1. Here, water is added in a small amount to prevent overheating, so that the compound 1 to be produced is not be burned.

In this step, glycine and phthalic anhydride are mixed with each other at a molar ratio of 1:1, followed by thoroughly stirring and distilled water is then added to the mixture, preferably in an amount of 10 to 30 ml. Here, if distilled water is added in an amount of less than 10 ml, the product can be burned by heat, since this reaction is the solid state reaction. If distilled water is added in an amount of more than 30 ml, the reaction rate is too slow. Therefore, about 20 ml of distilled water is most preferably added.

Also, the present invention is characterized in that the reaction of glycine and phthalic anhydride is performed by irradiation of microwaves. The heating reaction is preferably performed by irradiating microwaves at a frequency of 2.40 to 2.50 GHz (800 W), more preferably about 2.45 GHz, for 10 to 15 minutes. The irradiation time varies a little depending on the condition of the stirred reaction product and the amount of water. Preferably, the heating is performed until the solution of the reaction product becomes transparent. As soon as the heated solution of the reaction product is cooled, the compound 1 is produced.

If the condition of the microwave irradiation is less than the low limit of the specified range, the temperature of the inside of the reaction product is ununiform and thus, the reaction cannot sufficiently proceed, leading decrease in the yield of the compound 1. If the conditions of the microwave irradiation exceed the upper limit of the specified range, the temperature of the inside of the reaction product is rapidly increased and thus, the product can be burned.

Then, the produced compound 1 is dissolved in 500 to 1000 ml of ethanol to remove unreacted glycine. The compound 1 product is purified by recrystallization and dried to form white needle-shaped crystals of 2-(1,3-dioxoisoindolin-2-yl)acetic acid (compound 1).

In the present invention, the (G2) step is a step to produce 2-(1,3-dioxoisoindolin-2-yl)acetic chloride (compound 2) by adding thionylchloride ($SOCl_2$) to 2-(1,3-dioxoisoindolin-2-yl)acetic acid (compound 1), the product of the (G1) step.

In this step, thionylchloride ($SOCl_2$) is added in an amount of 1.5 to 3 mol per mol of 2-(1,3-dioxoisoindolin-2-yl)acetic acid (compound 1) and is preferably reacted, while stirring, at 70° C. for 2 to 3 hours under nitrogen atmosphere, provided with a reflux condenser. If thionylchloride ($SOCl_2$) is added in an amount of less than 1.5 mol, the compound 1 is not sufficiently dissolved and thus, can remain unreacted. If thionylchloride ($SOCl_2$) is added in an amount of more than 3 mol, the reaction time gets longer and the recovery time gets longer. After the reaction is completed, thionylchloride ($SOCl_2$) is preferably recovered by using an aspirator for recycling.

In the present invention, the (G3) step is a step to produce an N-alkyl-2-(1,3-dioxoisoindolin-2-yl)acetamide (compound 3) by reacting 2-(1,3-dioxoisoindolin-2-yl)acetic chloride (compound 2), produced in the (G2) step, with an alkylamine.

The alkylamine is preferably any one selected from the group consisting of octane-1-amine, nonan-1-amine, decan-1-amine, undecan-1-amine, dodecan-1-amine, tridecan-1-amine, tetradecan-1-amine, pentadecan-1-amine and hexadecan-1-amine.

Also, the N-alkyl-2-(1,3-dioxoisoindolin-2-yl)acetamide (compound 3) is preferably any one selected from the group consisting of N-octyl-2-(1,3-dioxoisoindolin-2-yl)acetamide, N-nonanyl-2-(1,3-dioxoisoindolin-2-yl)acetamide, N-decyl-2-(1,3-dioxoisoindolin-2-yl)acetamide, N-undecyl-2-(1,3-dioxoisoindolin-2-yl)acetamide, N-dodecyl-2-(1,3-dioxoisoindolin-2-yl)acetamide, N-tridecyl-2-(1,3-dioxoisoindolin-2-yl)acetamide, N-tetradecyl-2-(1,3-dioxoisoindolin-2-yl)acetamide, N-pentadecyl-2-(1,3-dioxoisoindolin-2-yl)acetamide, N-hexadecyl-2-(1,3-dioxoisoindolin-2-yl)acetamide.

In this step, the alkylamine is in a DMF mixture solution prepared by dissolving dodecylamine with triethylamine (TEA) in DMF. The DMF mixture solution is left in the ice bath. Then, a solution of 2-(1,3-dioxoisoindolin-2-yl)acetic chloride (compound 2) of the (G2) step dissolved in DMF is slowly added to the above DMF mixture solution, while stirring (exothermic reaction).

Here, alkylamine is preferably added in an amount of 1 mol per mol of 2-(1,3-dioxoisoindolin-2-yl)acetic chloride (compound 2). The DMF mixture solution is preferably prepared by mixing 1 mol of alkylamine and 3 to 10 mol of triethylamine in 10 to 20 mol of DMF (dimethylformamide) as a solvent.

After the reaction is completed, the DMF mixture solution is left for 3 to 24 hours. In order to separate the compound 3 surfactant in a pure form from the DMF mixture solution, the compound 3 surfactant which is free from a hydrophilic group since phthalic anhydride as a substituent is attached thereto is gelled by adding distilled water and separated by filtration. The filtered product is washed with distilled water at a temperature of 40 to 70° C. and dried. Here, distilled water is preferably added to the DMF mixture solution in an amount of 2 to 5 times of the volume of the DMF mixture solution.

In the present invention, the (G4) step is a step to synthesize 2-amino-N-alkylacetamide (compound 4) by adding ethanol and hydrazine ($NH_2NH_2$) to N-alkyl-2-(1,3-dioxoisoindolin-2-yl)acetamide (compound 3a), followed by heating. Here, 15 to 20 mol of ethanol and 5 to 10 mol of hydrazine ($NH_2NH_2$) as solvents are added to 1 mol of the product (compound 3) and heated at a temperature of 40 to 60° C. for 1 to 5 hours, while stirring. The by products are removed by filtration and the remaining filtrate is put into an aspirator to remove the solvents. The product is dissolved in methylene chloride. The by products are removed by filtration and the remaining filtrate is put into an aspiration to remove the solvents. The glycine-derived surfactant (compound 4) is recrystallized from n-hexane to improve the purity.

The glycine-derived surfactant (compound 4) synthesized according to the present invention has preferably 8 to 16 carbon atoms ($C_8$ to $C_{16}$).

Therefore, according to the present invention, in the (G1) step, the glycine-derived surfactant is synthesized by irradiating glycine and phthalic anhydride with microwaves.

Also, the method for synthesizing 2-amino-N-dodecylacetamide which is a glycine-derived surfactant according to the present invention will be described as follows.

Firstly, the method for synthesizing 2-amino-N-dodecylacetamide by using microwaves will be described in detail with reference to the following reaction scheme.

According to the present invention, the method for synthesizing 2-amino-N-dodecylacetamide comprises the steps of:

(G1a) irradiating a reaction product of glycine (a) and phthalic anhydride (b) with microwaves to produce 2-(1,3-dioxoisoindolin-2-yl)acetic acid (compound 1a);

(G2a) adding $SOCl_2$ as a solvent and a reactant to the compound 1 of step (G1) to produce 2-(1,3-dioxoisoindolin-2-yl)acetic chloride (compound 2a);

(G3a) allowing the compound 2 of step (G2) to react with dodecan-1-amine so as to product N-alkyl-2-(1,3-dioxoisoindolin-2-yl)acetamide (compound 3a), which is then gelled using distilled water and separated as a pure state; and (G4a) adding ethanol and $NH_2NH_2$ to the compound 3 of step (G3) to form a mixture, and then heating the mixture to synthesize 2-amino-N-alkylacetamide (compound 4a).

The 2-amino-N-dodecylacetamide is synthesized through the (G1a) to (G4a) steps of the following Reaction Scheme 2

[Reaction Scheme 2]

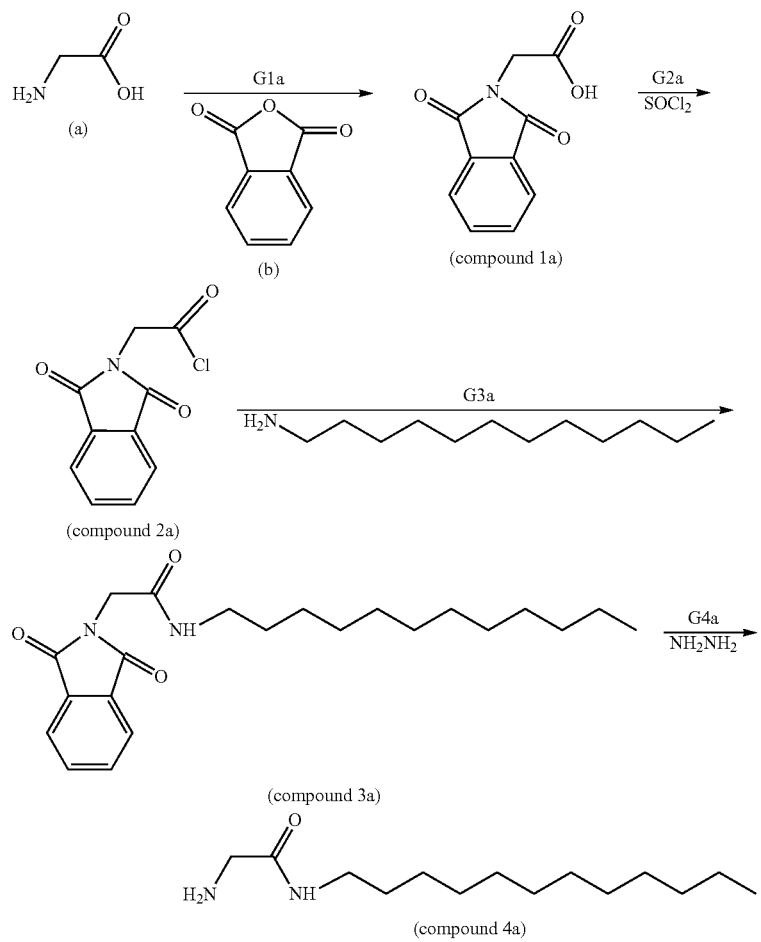

According to the present invention, since glycine (a) and phthalic anhydride (b) are reacted with each other by irradiation of microwaves in the (G1a) step, it is possible to increase the production yield of 2-(1,3-dioxoisoindolin-2-yl)acetic acid, the compound 1a and thereby, the synthesis yield of 2-amino-N-dodecylacetamide, the compound 4a, which is synthesized through the steps using the compound 1a.

In the present invention, the (G1a) step is a step to produce 2-(1,3-dioxoisoindolin-2-yl)acetic acid (compound 1a) by irradiating a reaction product of glycine (compound a) and phthalic anhydride (compound b) with microwaves. In this step, glycine having amine group and phthalic anhydride undergo the co-condensation reaction to produce the compound 1a. Here, water is added in a small amount to prevent overheating, so that the compound 1a to be produced is not be burned.

In this step, glycine and phthalic anhydride are mixed with each other at a molar ratio of 1:1, followed by thoroughly stirring and distilled water is then added to the mixture, preferably in an amount of 10 to 30 ml. Here, if distilled water is added in an amount of less than 10 ml, the product can be burned by heat, since this reaction is the solid state reaction. If distilled water is added in an amount of more than 30 ml, the reaction rate is too slow. Therefore, about 20 ml of distilled water is most preferably added.

Also, the present invention is characterized in that the reaction of glycine and phthalic anhydride is performed by irradiation of microwaves. The heating reaction is preferably performed by irradiating microwaves at a frequency of 2.40 to 2.50 GHz (800 W), more preferably about 2.45 GHz, for 10 to 15 minutes. The irradiation time varies a little depending on the condition of the stirred reaction product and the amount of water. Preferably, the heating is performed until the solution of the reaction product becomes transparent. As soon as the heated solution of the reaction product is cooled, the compound 1a is produced.

If the conditions of the microwave irradiation are less than the low limit of the specified range, the temperature of the inside of the reaction product is ununiform and thus, the reaction cannot sufficiently proceed, leading decrease in the yield of the compound 1a. If the conditions of the microwave irradiation exceed the upper limit of the specified range, the temperature of the inside of the reaction product is rapidly increased and thus, the product can be burned.

Then, the produced compound 1a is dissolved in 500 to 1000 ml of ethanol to remove unreacted glycine. The compound 1a product is purified by recrystallization and dried to form white needle-shaped crystals of 2-(1,3-dioxoisoindolin-2-yl)acetic acid (compound 1a).

In the present invention, the (G2a) step is a step to produce 2-(1,3-dioxoisoindolin-2-yl)acetic chloride (compound 2a) by adding thionylchloride ($SOCl_2$) to 2-(1,3-dioxoisoindolin-2-yl)acetic acid (compound 1a), the product of the (G1a) step.

In this step, thionylchloride ($SOCl_2$) is added in an amount of 1.5 to 3 mol per mol of 2-(1,3-dioxoisoindolin-2-yl)acetic acid (compound 1a) and is preferably reacted, while stirring, at 70° C. for 2 to 3 hours under nitrogen atmosphere, provided with a reflux condenser. If thionylchloride ($SOCl_2$) is added in an amount of less than 1.5 mol, the compound 1a is not sufficiently dissolved and thus, can remain unreacted. If thionylchloride ($SOCl_2$) is added in an amount of more than 3 mol, the reaction time gets longer and the recovery time gets longer. After the reaction is completed, thionylchloride ($SOCl_2$) is preferably recovered by using an aspirator for recycling.

In the present invention, the (G3a) step is a step to produce N-dodecyl-2-(1,3-dioxoisoindolin-2-yl)acetamide (compound 3a) by reacting 2-(1,3-dioxoisoindolin-2-yl)acetic chloride (compound 2a), produced in the (G2a) step, with dodecan-1-amine.

In this step, dodecylamine is in a DMF mixture solution prepared by dissolving dodecylamine with triethylamine (TEA) in DMF. The DMF mixture solution is left in the ice bath. Then, a solution of 2-(1,3-dioxoisoindolin-2-yl)acetic chloride (compound 2a) of the (G2a) step dissolved in DMF is slowly added to the above DMF mixture solution, while stirring (exothermic reaction).

Here, dodecylamine is preferably added in an amount of 1 mol per mol of 2-(1,3-dioxoisoindolin-2-yl)acetic chloride (compound 2a). The DMF mixture solution is preferably prepared by mixing 1 mol of dodecylamine and 3 to 10 mol of triethylamine in 10 to 20 mol of DMF (dimethylformamide) as a solvent.

After the reaction is completed, the DMF mixture solution is left for 3 to 24 hours. In order to separate the compound 3 surfactant in a pure form from the DMF mixture solution, the compound 3 surfactant which is free from a hydrophilic group since phthalic anhydride as a substituent is attached thereto is gelled by adding distilled water and separated by filtration. The filtered product is washed with distilled water at a temperature of 40 to 70° C. and dried. Here, distilled water is preferably added to the DMF mixture solution in an amount of 2 to 5 times of the volume of the DMF mixture solution.

In the present invention, the (G4a) step is a step to synthesize 2-amino-N-dodecylacetamide (compound 4a) by adding ethanol and hydrazine ($NH_2 NH_2$) to N-dodecyl-2-(1,3-dioxoisoindolin-2-yl)acetamide (compound 3a), followed by heating. Here, 15 to 20 mol of ethanol and 5 to 10 mol of hydrazine ($NH_2NH_2$) as solvents are added to 1 mol of the product (compound 3a) and heated at a temperature of 40 to 60° C. for 1 to 5 hours, while stirring. The by products are removed by filtration and the remaining filtrate is put into an aspirator to remove the solvents. The product is dissolved in methylene chloride. The by products are removed by filtration and the remaining filtrate is put into an aspiration to remove the solvents. 2-amino-N-dodecylacetamide, (compound 4a) is recrystallized from n-hexane to improve the purity.

The 2-amino-N-dodecylacetamide (compound 4a) synthesized according to the present invention has preferably 6 to 16 carbon atoms ($C_6$ to $C_{16}$).

Therefore, according to the present invention, in the (G1a) step, 2-amino-N-dodecylacetamide is synthesized by irradiating glycine and phthalic anhydride with microwaves.

Hereinafter, the present invention will be described in further detail with reference to the following examples, but the scope of the present invention is not limited to these examples.

EXAMPLES

Example 1

Synthesis of 2-amino-N-dodecylacetamide by Irradiation of Microwaves in the (G1a) Step In the (G1a) step, glycine and phthalic anhydride were mixed with each other at a molar ratio of 1:1, followed by thoroughly stirring and 20 ml of distilled water was then added to the mixture. The mixture solution was heated by irradiating microwaves at a frequency of 2.45 GHz (800 W) for 10 minutes, until the solution of the reaction product became transparent. As soon as the heated solution of the reaction product was cooled, the product was formed as white needle-shaped crystals. The white crystals were dissolved in 800 ml of heated ethanol, while stirring. Here, the unreacted glycine was removed with a filter (Yield 99%).

The remaining filtrate was allowed to stand at room temperature for 3 days to obtain white needle-shaped crystals of 2-(1,3-dioxoisoindolin-2-yl)acetic acid (compound 1a) (Yield 80%).

In the (G2a) step, 2 mol of thionylchloride ($SOCl_2$) was added to the compound 1a to produce 2-(1,3-dioxoisoindolin-2-yl)acetic chloride (compound 2a) and the unreacted thionylchloride ($SOCl_2$) was recovered by using an aspirator.

In the (G3a) step, the compound 2a of the step (G2a) was added to the DMF mixture solution prepared by dissolving dodecylamine with triethylamine (TEA) in DMF. After the reaction was left for 5 hours, distilled water was added at a volume ratio of 3:1 to the DMF mixture solution to gel the surfactant of N-dodecyl-2-(1,3-dioxoisoindolin-2-yl)acetamide (compound 3a), followed by filtration. The filtered product was washed with distilled water at 60° C. and dried. Here, the DMF mixture solution was used in a molar ratio of 2-(1,3-dioxoisoindolin-2-yl)acetic chloride (compound 2a) to dodecylamine of 1:1, in which the DMF mixture solution was prepared by mixing 1 mol of dodecylamine and 7 mol of triethylamine (TEA) in 15 mol of DMF (dimethylformamide).

Figure 2:
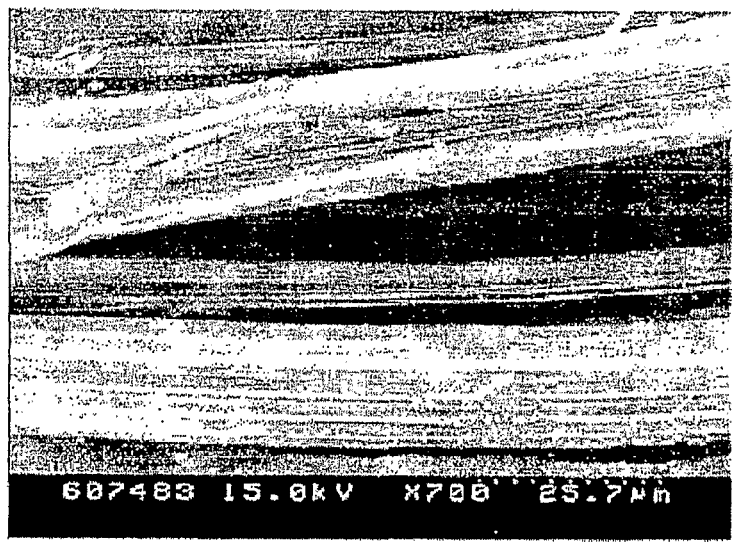
FIG. 2 is a SEM photograph showing 2-amino-N-dodecylacetamide of Example 1.
Figure 3:
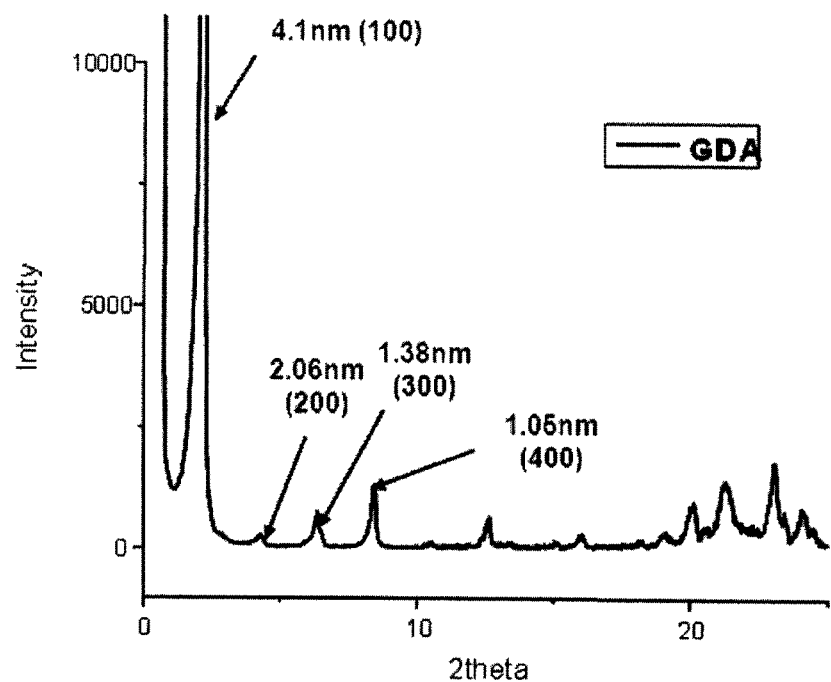
FIG. 3 is a graph showing the XRD result of 2-amino-N-dodecylacetamide.

In the (G4a) step, 15 mol of ethanol and 5 mol of hydrazine ($NH_2NH_2$) were added to 1 mol of N-dodecyl-2-(1,3-dioxoisoindolin-2-yl)acetamide (the compound 3a) of the step (G3a) and heated at 50° C. for 3 hours, while stirring. The by-products were removed by filtration and the filtrate was put into an aspirator to remove ethanol. The product was dissolved in methylene chloride to remove the by-products and recrystallized from n-hexane to synthesize 2-amino-N-dodecylacetamide (compound 4a) (Yield 50%). The product was confirmed as 2-amino-N-dodecylacetamide by $^1$H-NMR, as shown in FIG. 1, the SEM, as shown in FIG. 2 and XRD, as shown in FIG. 3.

Comparative Example 1

Synthesis of 2-amino-N-dodecylacetamide by Hydrothermal Method

In (G1a) step, 0.1 mol of glycine and 0.1 mol of phthalic anhydride were added to 1000 ml of a mixture of benzene of toluene (1:1) and stirred at 150° C. for 4 hours, at reflux. Here, in order to remove water produced during the synthesis, the Dean-Stock Column was used. After the reaction was cooled, crystals were obtained (Yield 50%). The white crystals were dissolved in 800 ml of heated ethanol, while stirring and unreacted glycine crystals which has not been dissolved were removed using a filter. The filtrate was left at room temperature for 3 days to obtain 2-(1,3-dioxoisoindolin-2-yl)acetic acid (compound 1a) as white needle-shaped crystals (Yield 40%).

Figure 4:
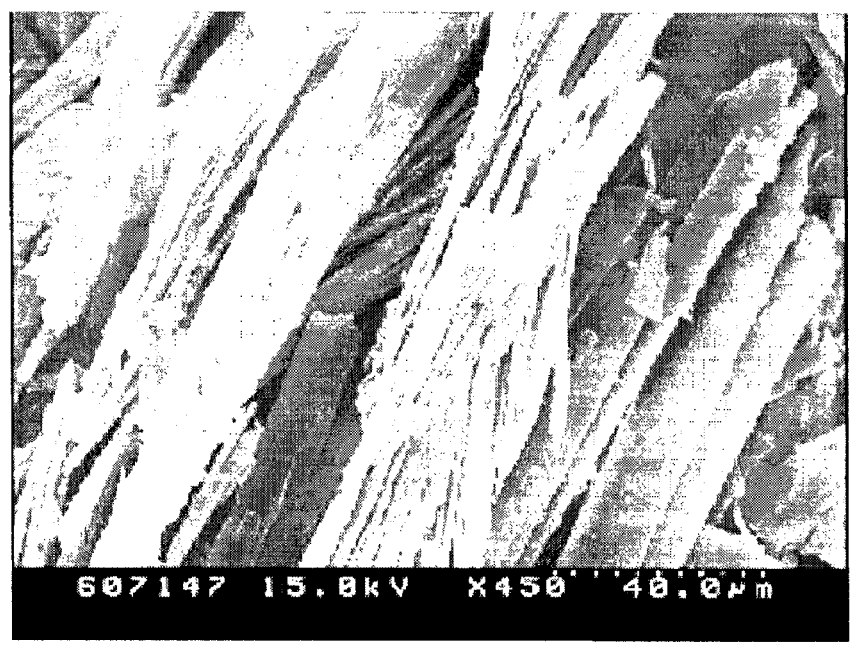
FIG. 4 is a SEM photograph showing 2-amino-N-dodecylacetamide synthesized in Comparative Example 1.

The (G2a) to (G4a) steps were performed by the same method as described in Example 1 to synthesis 2-amino-N-dodecylacetamide (compound 4a) (Yield 25%). Here, the product was confirmed as 2-amino-N-dodecylacetamide by ¹H-NMR, as shown in FIG. 1, XRD, as shown in FIG. 3 and SEM, as shown in FIG. 4.

As shown in the result of Example 1 and Comparative Example 1, the yield of 2-(1,3-dioxoisoindolin-2-yl)acetic acid (compound 1a) synthesized in the (G1a) step was 80% for Example 1 and 40% for Comparative Example 1. Therefore, it was noted that the yield of the compound 1a of Example 1 was much higher than Comparative Example 1.

Meanwhile, referring to the yield of 2-amino-N-dodecylacetamide (compound 4a), the final product of the synthesis method according to the present invention, Example 1 was 50%, because the yield of the compound 1a was high, and Comparative Example 1 was 25%. Thus, it was noted that yield of the compound 4a was also much higher in Example 1 than Comparative Example 1.

Therefore, it was confirmed that the method for synthesizing 2-amino-N-dodecylacetamide of Example 1 according to the present invention showed a high yield, thereby improved productivity.

2. Synthesis of One-Dimensional Helical Nanoporous Structures

Example 2

2-amino-N-dodecylacetamide synthesized by the method of Example 1 was mixed with 1 mmol of gel-generator in 20 ml of water and heated at 60° C. until the solution became transparent. 4 mmol of tetraethoxyorthosilicate (TEOS) was added to the solution and heated at 60° C. until the solution became transparent. The solution was kept in the static condition for 3 days. Then, 10 ml of ethanol was added thereto to wash the ceramic precursor mixture. 2-amino-N-dodecylacetamide was recovered and calcined at 550° C. for 6 hours to synthesize the one-dimensional helical nanoporous structures.

Example 3

One-dimensional helical nanoporous structures were synthesized by the same method as described in Example 2 except that 10 mmol of tetraethoxyorthosilicate (TEOS) was added.

Figure 5:
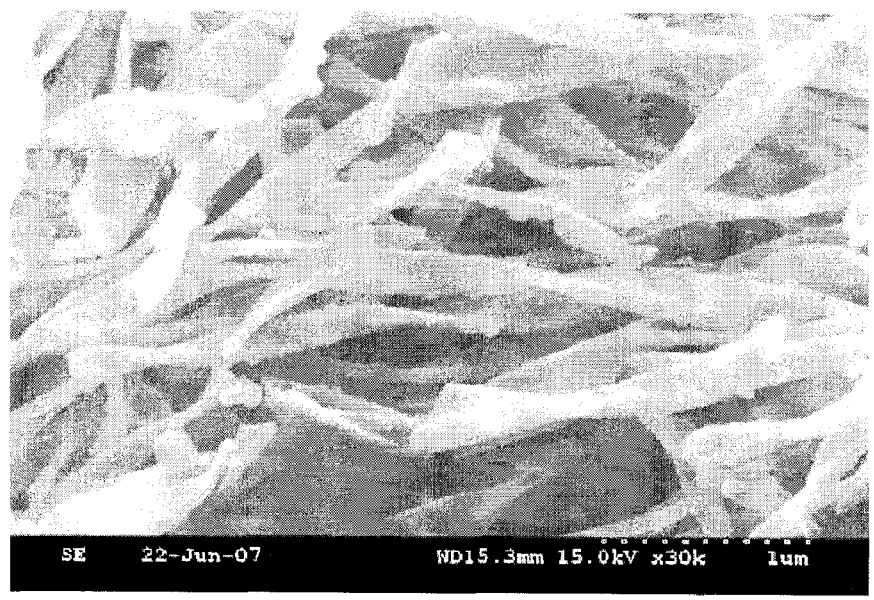
FIG. 5 is a SEM photograph of the helical nanoporous structures having a pore size of 2 to 5 nm synthesized in Example 2 according to the present invention.

In the SEM analysis of crystals of the one-dimensional helical nanoporous structures synthesized in Example 2, it was confirmed that the crystals are one-dimensional helical nanoporous structures having a pore size of 2 to 5 nm, a outer diameter of about 20 nm and a inner diameter of 3 to 4 nm, as shown in FIG. 5.

In the Nitrogen sorption analysis according to Barrett, Joyner and Halenda's method, it was confirmed that the structures had a BET surface area of 584 m³/g, a pore volume of 0.95 cm³/g and a pore size of 2.8 nm.

Figure 6:
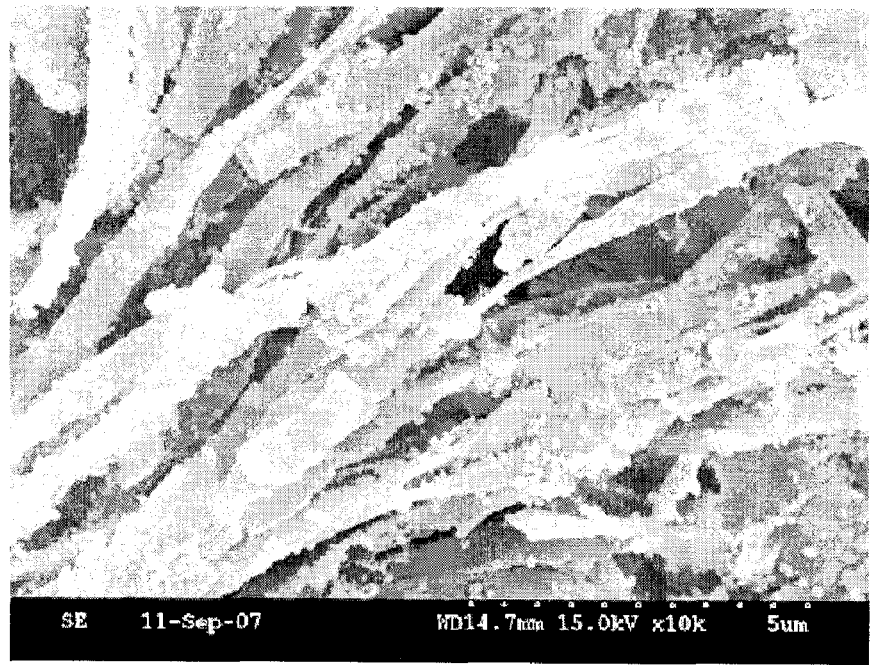
FIG. 6 is a SEM photograph of the helical nanoporous structures having a pore size of 2 to 5 nm synthesized in Example 3 according to the present invention.

Also, in the SEM analysis of crystals of the one-dimensional helical nanoporous structures synthesized in Example 3, it was confirmed that the crystals are one-dimensional helical nanoporous structures having a pore size of 2 to 5 nm, a outer diameter of about 20 nm and a inner diameter of 3 to 4 nm, as shown in FIG. 6.

In the Nitrogen sorption analysis according to Barrett, Joyner and Halenda's method, it was confirmed that the structures had a BET surface area of 582 m³/g, a pore volume of 0.94 cm³/g and a pore size of 2.7 nm.

Although the present invention has been described with reference to preferred embodiments, it will be understood by those skilled in the art that numerous variants and modifications may be made in the art without departing from the spirit and scope of the invention as set forth in the appended claims.

MODE FOR THE INVENTION

To accomplish the above objects, in one aspect, the present invention provides a method for synthesizing one-dimensional helical nanoporous structures, the method comprising the steps of: (1) heating an aqueous solution, obtained by adding a template to water, until the aqueous solution becomes transparent; (2) adding a ceramic precursor to the template-containing aqueous solution of step (1), and then heating the aqueous solution until it becomes transparent; (3) allowing the heated aqueous solution of step (2) to stand to form a gelled mixture; (4) washing the gelled mixture of step (3) with alcohol to remove the template; and (5) calcining the washed mixture of step (4) from which the alcohol and the template have been removed.

In the step (1), the template has a glycine-derived surfactant having the following chemical structure:

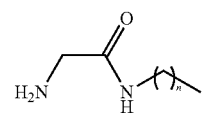

wherein n is preferably an integer ranging from 7 to 15.

In another aspect, the present invention also provides a method for synthesizing a glycine-derived surfactant for synthesizing one-dimensional helical nanoporous structures, the method comprising the steps of: (G1) irradiating a reaction product of glycine (a) and phthalic anhydride (b) with microwaves to produce 2-(1,3-dioxoisoindolin-2-yl)acetic acid (compound 1); (G2) adding $SOCl_2$ to the compound 1 of step (G1) to produce 2-(1,3-dioxoisoindolin-2-yl)acetic chloride (compound 2); (G3) allowing the compound of step (G2) to react with alkylamine so as to product N-alkyl-2-(1,3-dioxoisoindolin-2-yl)acetamide (compound 3); and (G4) adding ethanol and $NH_2NH_2$ to the compound 3 of step (G3) to form a mixture, and then heating the mixture to synthesize 2-amino-N-alkylacetamide (compound 4).

In step (G1), microwaves are irradiated at a frequency (800 W) of 2.40-2.50 GHz for 10-15 minutes to heat the reaction product.

INDUSTRIAL APPLICABILITY

The present invention relates to a method for synthesizing one-dimensional helical nanoporous structure, in which a self-assembled structure of a glycine-derived surfactant is used as a template at room temperature to synthesize the one-dimensional helical mesoporous silica structures having a uniform pore size and a method for synthesizing a glycine-derived surfactant for synthesizing the helical nanoporous structures, in which the glycine-derived surfactant is synthesized by irradiation of microwaves.

What is claimed is:
1. A method for synthesizing one-dimensional helical nanoporous structures, the method comprising the steps of:
   1) heating an aqueous solution, obtained by adding a template to water, until the aqueous solution becomes transparent;

2) adding a ceramic precursor to the template-containing aqueous solution of step 1), and then heating the aqueous solution until it becomes transparent;
3) allowing the heated aqueous solution of step 2) to stand to form a gelled mixture;
4) washing the gelled mixture of step 3) with alcohol to remove the template; and
5) calcining the washed mixture of step 4) from which the alcohol and the template have been removed, wherein the template in step 1) has a glycine-derived surfactant having the following chemical structure:

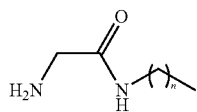

wherein n is an integer ranging from 7 to 15.

2. The method of claim 1, wherein the ceramic precursor is one or more selected from the group consisting of silica precursors including TEOS (tetraethoxysilane), TBOS (tetrabutyl orthosilicate), TMOS (teramethoxysilane) and SiCl4 (tetrchlorosilane), $TiO_2$ precursors including titanium (IV) butoxide, titanium (IV) isopropoxide and titanium (IV) chloride, $SnO_2$ precursors including tin (IV) chloride and tin (IV) tert-butoxide, $ZnO_2$ precursors including zinc acetate and zinc chloride, and $ZrO_2$ precursors including zirconium (IV) t-butoxide, zirconium (IV) chloride, zirconium (IV) ethoxide and zirconium (IV) propoxide.

3. The method of claim 1, wherein the ceramic precursor in step 2) is added in an amount of 4-10 mmol per mmole of the glycine-derived surfactant.

4. The method of claim 3, wherein the one-dimensional helical nanoporous structures have a pore size of 2-5 nm.

5. The method of claim 2, wherein the one-dimensional helical nanoporous structures have a pore size of 2-5 nm.

6. The method of claim 1, wherein the one-dimensional helical nanoporous structures have a pore size of 2-5 nm.

7. The method of claim 1, wherein the one-dimensional helical nanoporous structures have a pore size of 2-5 nm.

* * * * *